(12) United States Patent
Torihara et al.

(10) Patent No.: US 6,624,331 B1
(45) Date of Patent: Sep. 23, 2003

(54) PROCESS FOR THE PREPARATION OF BENZYLOXYACETALDEHYDE

(75) Inventors: Masahiro Torihara, Niigata (JP); Kensuke Nagashima, Niigata (JP); Koichi Kanehira, Kurashiki (JP); Yoshin Tamai, Niigata (JP)

(73) Assignee: Kuraray Co., Ltd., Kurashiki (JP)

( * ) Notice: Subject to any disclaimer, the term of this patent is extended or adjusted under 35 U.S.C. 154(b) by 0 days.

(21) Appl. No.: 09/926,229

(22) PCT Filed: Mar. 28, 2000

(86) PCT No.: PCT/JP00/01888

§ 371 (c)(1),
(2), (4) Date: Sep. 27, 2001

(87) PCT Pub. No.: WO00/59857

PCT Pub. Date: Oct. 12, 2000

(30) Foreign Application Priority Data

Apr. 2, 1999 (JP) .............................. 11-095739

(51) Int. Cl.$^7$ .................. C07C 45/00; C07C 47/56
(52) U.S. Cl. .................. 568/437; 568/426; 568/442
(58) Field of Search ................ 568/426, 437, 568/442

(56) References Cited

U.S. PATENT DOCUMENTS 5,118,833 A    6/1992   Mori et al.

FOREIGN PATENT DOCUMENTS

| EP | 0 412 378 | 2/1991 |
|----|-----------|--------|
| EP | 412378    | 2/1991 |
| JP | 3-58956   | 3/1991 |
| JP | 5-310632  | 11/1993 |
| JP | 07-330654 | 12/1995 |
| JP | 7-330654  | 12/1995 |
| JP | 08-176053 | 7/1996 |

| WO | 01-02333 | 1/2001 |

OTHER PUBLICATIONS

D. F. Taber, et al., J. Org. Chem., vol. 59, No. 20, pp. 6014–6017, "Intramolecular C–H Insertion By An Alkylidene Carbene: Diastereoselective Synthesis of a Taxol a Ring Synthon", 1994.
J. A. Marshall, et al., J. Org. Chem., vol. 51, No. 9, pp. 1633–1635, "A Stereoselective Synthesis of the Hydronaphthalene Substructure of Kijanolide", 1986.
D.F. Taber, et al., "Interamolecular C–H Insertion by an Alkylidene Carbene: Diastereoselective Synthesis of a Taxol A Ring Synthon," J. Org. Chem., 1994, vol. 59, No. 20, pp. 6014–6017.
J.A. Marshall, et al., "A Stereoselective Synthesis of the Hydronaphthalene Substructure of Kijanolide," J. Org. Chem., 1986, vol. 51, No. 9, pp.1633–1635.
R. J. Parry et al J. Amer. Chem Soc 104, 3217 (1982).*
D. Craig et al Tetrahedron Lett 33, 7445 1992.*

* cited by examiner

Primary Examiner—Paul J. Killos
(74) Attorney, Agent, or Firm—Oblon, Spivak, McClelland, Maier & Neustadt, P.C.

(57) ABSTRACT

A process for producing benzyloxyacetaldehyde which comprises oxidizing 2-benzyloxyethanol with hypochlorous acid in the presence of a nitroxy radical having the general formula (I)

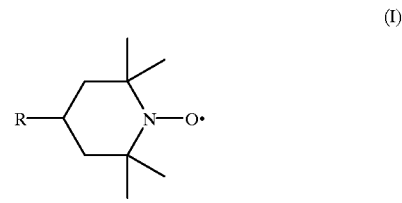

wherein R represents a hydrogen atom, an acyloxy group, an alkoxyl group or an aralkyloxy group.

17 Claims, No Drawings

PROCESS FOR THE PREPARATION OF BENZYLOXYACETALDEHYDE

TECHNICAL FIELD

The present invention relates to a process for producing benzyloxyacetaldehyde. The benzyloxy-acetaldehyde obtained by the present invention is a useful compound as a starting material for synthesizing pharmaceuticals and agricultural chemicals.

BACKGROUND ART

Known processes for producing benzyloxyacetaldehyde are as follows.

(1) Process which comprises oxidizing 2-benzyloxy-ethanol with dimethyl sulfoxide (DMSO).

(a)

wherein Bn represents a benzyl group.
[See D. Taber, et al., J. Org. Chem., 59, 6014(1994)]

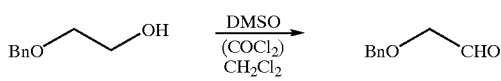

(b)

wherein Bn is as defined above.
[See J. A. Marshall, et al., Tetrahedron Lett., 29, 913(1988)]

(c)

wherein Bn is as defined above, and DCC is an abbreviation of dicyclocarbodiimide.
[See R. J. Parry, et. al, J. Am. Chem. Soc. 104,3217 (1982)]

(2) Process which comprises oxidizing 1,4-dibenzyloxy-2-butene with ozone. [See WO98/29395]

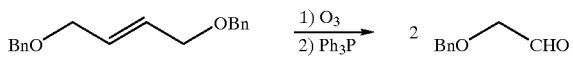

wherein Bn is as defined above.

(3) Process which comprises oxidizing allyl benzyl ether with ozone. [See D. Craig, et al., Tetrahedron Lett., 33, 7445(1992)]

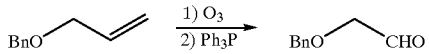

wherein Bn is as defined above.

(4) Process which comprises oxidizing 1,4-dibenzyloxy-2,3-dihydroxybutane with periodic acid. [See Y.-L. Zhong, et al., J. Org. Chem., 62, 2622(1997)]

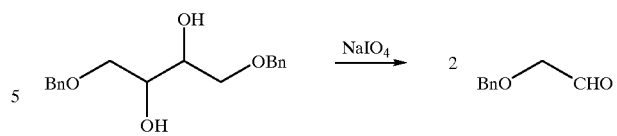

wherein Bn is as defined above.

(5) Process which comprises oxidizing 1-benzyl-glycerine with periodic acid. [See M. J. Shiao, et al., Synth. Commun., 18, 359(1988)]

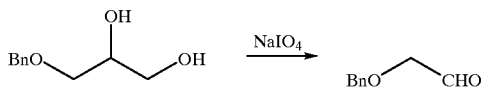

wherein Bn is as defined above.

(6) Process which comprises using a 2-halogenated acetaldehyde derivative as a starting material. [See L. -S. Hsu, et al., Heterocycles, 43, 2687(1996)]

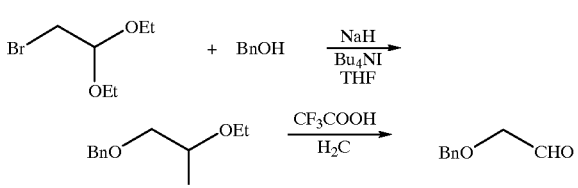

wherein Bn is as defined above.

(7) Process which comprises benzylating and hydrolyzing 2-hydroxyacetaldehyde diethyl ether. [See J. Barber, J. Labelled Compd. , Radiopharm. , 22, 229(1985)]

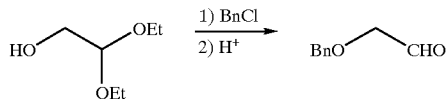

wherein Bn is as defined above.

(8) Process which comprises reducing a benzyloxyacetic acid ester with hydrogenated diisobutylaluminum (DIBAL). [See Japanese Patent Publication No. 33381/1995]

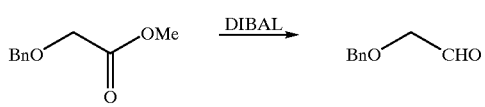

wherein Bn is as defined above.

(9) Process which comprises subjecting phenyl-2-benzyloxyethyl sulfoxide to the Pummerer reaction.
[See H. Sugihara, et al., Synthesis, 881(1978)]

-continued

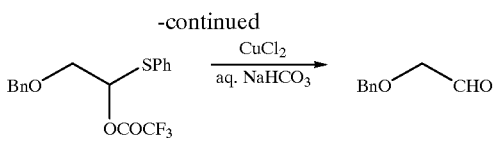

wherein Bn is as defined above.

However, these processes have the following draw-backs.

The process (1) of oxidation with DMSO, which byproduces the same moles of dimethyl sulfide as those of the starting material, is not preferable from the environmental viewpoint.

The processes (2) and (3) of oxidation with ozone, that is difficult to handle on a commercial scale, yield intermediate products of unstable ozonides, thereby causing a problem on safety.

The processes (4) and (5), using periodic acid, require that the expensive periodic acid be used in an amount of at least one molar equivalent relative to the starting material.

The processes (6) and (7) use as starting materials 2-halogenated acetaldehyde diethylacetal and 2-hydroxyacetaldehyde diethylacetal, respectively, which are both relatively expensive.

The process (8) uses as a reducing agent DIBAL, which is expensive and tends to ignite on contact with air, thus having a problem on safety.

The process (9) is difficult to commercialize, since the synthesis of the starting material phenyl-2-benzyl-oxyethyl sulfoxide requires multi-stage reactions.

Accordingly, an object of the present invention is to provide a process for producing benzyloxyacetaldehyde commercially advantageously from a starting material that is easy to handle and commercially available at a low cost.

DISCLOSURE OF THE INVENTION

According to the present invention, the above object can be achieved by providing a process for producing benzyloxyacetaldehyde, which comprises oxidizing 2-benzyloxyethanol with hypochlorous acid in the presence of a nitroxy radical having the general formula (I) [hereinafter referred to as "nitroxy radical (I)"]

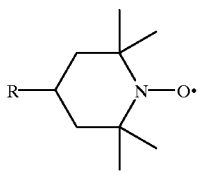

(I)

Wherein R represents a hydrogen atom, an acyloxy group, an alkoxyl group or an aralkyloxy group.

BEST MODE FOR CARRYING OUT THE INVENTION

In the above general formula, examples of the acyloxy group that may be represented by R are acetoxy, propionyloxy and benzoyloxy; examples of the alkoxyl group are methoxy and ethoxy; and examples of the aralkyloxy group are benzyloxy.

Examples of the nitroxy radical (I) are 2,2,6,6-tetramethylpiperidinyl-1-oxy, 4-acetoxy -2,2,6,6-tetramethylpiperidinyl-1-oxy, 4-methoxy -2,2,6,6-tetramethylpiperidinyl-1-oxy and 4-benzyloxy -2,2,6,6-tetramethylpiperidinyl-1-oxy.

The nitroxy radical (I) is desirably used in an amount of 0.05 to 10 mole % based on the moles of 2-benzyloxyethanol, more preferably 0.1 to 0.5 mole % on the same basis in view of reactivity and economy.

Hypochlorous acid, available in the form of an aqueous solution, may be used as it is. It is, however, desirable in the present invention, to use hypochlorous acid as generated in the reaction zone, since the aqueous solution of hypochlorous acid is unstable. Although hypochlorous acid may be generated in the reaction zone by any process with no particular limitation, it is desirable to generate it from a stable and commercially readily available hypochlorite compound, e.g. sodium hypochlorite, potassium hypochlorite and bleaching powder.

Of these hypochlorite compounds, sodium hypochlo-rite is particularly preferred, since it is readily available in large amounts at a low cost in the form of an aqueous solution having a concentration of 12 to 13% and can be handled easily. The aqueous sodium hypochlo-rite may be used as purchased or after dilution to an appropriate concentration. Where a solid-form hypo-chlorite, such as bleaching powder, is used, it may be used as it is or in the form of, after dissolution in water, aqueous solution having a concentration in a range of 5 to 20%.

Concrete examples of processes of generating hypochlorous acid from a hypochlorite compound include a process which comprises reacting the hypochlorite compound with a compound capable of reacting therewith to generate hypochlorous acid, such as a hydrogen carbonate, e.g. sodium hydrogen carbonate and potassium hydrogen carbonate; a mineral acid, e.g. hydrochloric acid, sulfuric acid, boric acid and phosphoric acid; an organic acid, e.g. acetic acid, propionic acid, benzoic acid and toluenesulfonic acid; a phosphate, e.g. potassium dihydrogen phosphate, dipotassium hydrogen phosphate, sodium dihydrogen phosphate and disodium hydrogen phosphate; and potassium hydrogen phthalate. These compounds capable of reacting with a hypochlorite compound to generate hypochlorous acid are used desirably in an amount of 5 to 25 mole % based on the moles of the hypochlorite compound. These compounds capable of reacting with a hypochlorite compound to generate hypochlorous acid may either be used as they are or after solution in or dilution with water.

The amount of hypochlorous acid used is, in view of the yield of the reaction and productivity, desirably in a range of 0.5 to 1 molar equivalent relative to the moles of 2-benzyloxyethanol. If hypochlorous acid is used in an amount exceeding 1 molar equivalent, the benzyloxyacetaldehyde that forms will tend to be further oxidized under the same reaction conditions into the corresponding carboxylic acid, thereby decreasing the yield. On the other hand, if the amount of hypochlorous acid used is less than 1 molar equivalent, the conversion of 2-benzyloxyethanol will decrease with decreasing amount of the acid. Although unreacted 2-benzyloxy-ethanol can be recovered by isolation and purification procedures and be used again, the amount of hypochlorous acid of less than 0.5 molar equivalent will decrease the yield of benzyloxyacetaldehyde, which is disadvantageous from the viewpoint of productivity.

The process of the present invention can be carried out either in the presence or absence of a solvent. Examples of usable solvents, which are not particularly limited as long as the reaction is not adversely affected, aromatic hydrocarbons, e.g. toluene, xylene and mesitylene; halogenated hydrocarbons, e.g. dichloromethane, chloroform, carbon tetrachloride and 1,2-dichloroethane; ethers, e.g. diethyl ether, diisopropyl ether and methyl tertiary butyl ether; ketones, e.g. methyl isobutyl ketone and methyl tertiary butyl ketone; and water. These solvents may either be used singly or in combination of 2 or more. On use of a solvent, its amount is not particularly limited, but, in general, the amount is preferably in a range of 1 to 10 parts by weight based on one part by weight of 2-benzyloxyethanol.

The reaction temperature is preferably in a range of −5 to 50° C. and, in view of the stability of hypochlorous acid in the reaction zone, more preferably in a range of 0 to 30° C.

The reaction is carried out by, for example, preparing a solution by mixing prescribed amounts of 2-benzyloxyethanol, nitroxy radical (I), a compound capable of generating hypochlorous acid on reaction with the hypochlorite compound used and, as necessary, a solvent, adjusting the temperature at a prescribed level, and adding to the mixed solution thus prepared the hypochlorite compound by small amounts.

The benzyloxyacetaldehyde thus obtained can be isolated and purified by the usual isolation and purification procedure employed in organic synthesis. For example, a reducing agent such as sodium thiosulfate is added to the reaction mixture to decompose the remaining hypochlorous acid and the organic layer is separated. The organic layer is then washed with water or, preferably, saturated aqueous solution of sodium chloride, and the solvent is removed, to obtain a crude product, which is then purified by column chromatography or like means. On this purification procedure, unreacted 2-benzyloxyethanol can be recovered.

Hereinbelow, the present invention is described more concretely by reference to Examples, which are by no means limitative of the invention.

EXAMPLE 1

A 300-ml three-necked flask was charged with 15.2 g (0.1 mole) of 2-benzyloxyethanol, 100 ml of dichloromethane and 20 ml of water, and further with 2.6 g (15 mmoles) of dipotassium hydrogenphosphate and 32 mg (0.15 mmole) of 4-acetoxy-2,2,6,6-tetramethyl-piperidinyl-1-oxy, and the mixture was cooled with ice water to 0 to 5° C. with stirring. To the mixed solution, with stirring, 46.6 g (75 mmoles) of a 12% aqueous solution of sodium hypochlorite was added dropwise over 2 hours, while care was being taken not to permit the temperature to exceed 20° C. After completion of the addition, the mixture was stirred at the same temperature for 30 minutes. To the obtained mixture, 30 ml of a 5% aqueous solution of sodium thiosulfate was added, and the resulting mixture was stirred for 5 minutes. The organic layer was then separated from the mixture. The organic layer separated was washed with 30 ml of saturated aqueous solution of sodium chloride and the solvent was distilled off. The residue obtained was further subjected to vacuum distillation, to yield 7.5 g of benzyloxyacetaldehyde as a fraction at a boiling point of 118 to 120° C./13 mmHg and 4.6 g of unreacted 2-benzyloxyacetaldehyde as a fraction at a boiling point of 128 to 130° C./13 mmHg (yield of benzyloxyacetaldehyde based on the 2-benzyloxyethanol that had reacted: 71.4%, ratio of recovery of 2-benzyloxyethanol: 30.2%).

EXAMPLE 2

Example 1 was repeated except that 2.5 g (30 mmoles) of sodium hydrogen carbonate was used instead of 2.6 g (15 mmoles) of dipotassium hydrogen phosphate, to obtain 7.1 g of benzyloxyacetaldehyde and 4.5 g of 2-benzyloxyethanol (yield of benzyloxyacetaldehyde based on the 2-benzyloxyethanol that had reacted: 66.8%, ratio of recovery of 2-benzyloxyethanol: 29.6%).

EXAMPLE 3

Example 1 was repeated except that 100 ml of toluene was used instead of 100 ml of dichloromethane, to obtain 7.2 g of benzyloxyacetaldehyde and 4.5 g of 2-benzyloxyethanol (yield of benzyloxyacetaldehyde based on the 2-benzyloxyethanol that had reacted: 68.2%, ratio of recovery of 2-benzyloxyethanol: 29.6%).

EXAMPLE 4

Example 1 was repeated except that 100 ml of methyl isobutyl ketone was used instead of 100 ml of dichloromethane, to obtain 7.6 g of benzyloxyacetaldehyde and 5.5 g of 2-benzyloxyethanol (yield of benzyloxyacetaldehyde based on the 2-benzyloxyethanol that had reacted: 79.5%, ratioof recoveryof2-benzyloxyethanol: 36.3%).

Industrial Applicability

According to the present invention, benzyloxyacetaldehyde can be produced commercially advantageously from a starting material that is easy to handle and commercially available at a low cost. The benzyloxyacetaldehyde obtainable by the present invention is a compound useful as a starting material for pharmaceuticals and agricultural chemicals.

What is claimed is:

1. A process for producing benzyloxyacetaldehyde, which comprises oxidizing 2-benzyloxyethanol with hypochlorous acid in the presence of a nitroxy radical having the general formula (I)

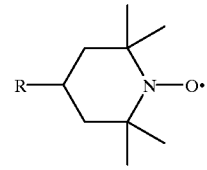

(I)

wherein R represents a hydrogen atom, an acyloxy group, an alkoxyl group or an aralkyloxy group.

2. The process according to claim 1, wherein said hypochlorous acid is generated in the reaction zone.

3. The process according to claim 1, wherein R is an acyloxy group selected from acetoxy, propionyloxy, and benzoyloxy.

4. The process according to claim 1, wherein R is a alkoxyl group selected from the group consisting of methoxy and ethoxy.

5. A process according to claim 1, wherein R is benzyloxy.

6. The process according to claim 1, wherein the nitroxy radical (I) is at least one member selected from the group consisting of 2,2,6,6-tetramethylpiperidinyl-1-oxy, 4-acetoxy-2,2,6,6-tetramethylpiperidinyl-1-oxy, 4-methoxy-2,2,6,6-tetramethylpiperidinyl-1-oxy and 4-benzyloxy-2,2,6,6-tetramethylpiperidinyl-1-oxy.

7. The process according to claim 1, wherein the nitroxy radical is present in an amount ranging from 0.05 to 10 mol % based on the moles of 2-benzyloxyethanol.

8. The process according to claim 1, wherein said hypochlorous acid is present at a concentration in the range of from 0.5 to 1 molar equivalent relative to the moles of 2-benzyloxyethanol.

9. The process according to claim 1, wherein said process is carried out in the presence of a solvent.

10. The process according to claim 9, wherein said solvent is at least one member selected from the group consisting of an aromatic hydrocarbon, a halogenated hydrocarbon, an ether, a ketone, and water.

11. The process according to claim 10, wherein said solvents are present in an amount ranging from 1 to 10 parts by weight based on one part by weight of 2-benzyloxyethanol.

12. The process according to claim 1, wherein said oxidizing is performed at a temperature in a range of from −5 to 50° C.

13. The process according to claim 2, wherein said hypochlorous acid is generated from a hypochlorite compound.

14. The process according to claim 13, wherein said hypochlorite compound is sodium hypochlorite, potassium hypochlorite, and bleaching powder.

15. The process according to claim 13, wherein said hypochlorite compound is present in an aqueous solution at a concentration ranging from 5 to 20%.

16. The process according to claim 13, wherein said hypochlorite compound is reacted with at least one member selected from the group consisting of a hydrogen carbonate, a mineral acid, an organic acid, and a phosphate.

17. The process according to claim 2, wherein said hypochlorous acid is present in an amount of from 5 to 25 mol % based on the moles of the hypochlorite compound.

* * * * *